United States Patent [19]

François et al.

[11] Patent Number: 5,707,975
[45] Date of Patent: Jan. 13, 1998

[54] ORAL FORMULATIONS ON AN ANTIFUNGAL

[75] Inventors: Marc Karel Jozef François, Kalmthout; Willy Maria Albert Carlo Dries, Merksplas, both of Belgium

[73] Assignee: Janssen Pharmaceutica, N.V., Beerse, Belgium

[21] Appl. No.: 604,950

[22] PCT Filed: Sep. 22, 1994

[86] PCT No.: PCT/EP94/03169

§ 371 Date: Feb. 22, 1996

§ 102(e) Date: Feb. 22, 1996

[87] PCT Pub. No.: WO95/08993

PCT Pub. Date: Apr. 6, 1995

[51] Int. Cl.$^6$ ............................................ A61K 9/127
[52] U.S. Cl. ..................................... 514/58; 514/252
[58] Field of Search ................ 514/252, 58; 536/163

[56] References Cited

U.S. PATENT DOCUMENTS

| | | | |
|---|---|---|---|
| 3,459,731 | 8/1969 | Gramera et al. | 260/209 |
| 4,267,179 | 5/1981 | Heeres et al. | 424/25 |
| 4,383,992 | 5/1983 | Lipari | 424/238 |
| 4,659,696 | 4/1987 | Hirai et al. | 514/15 |
| 4,764,604 | 8/1988 | Muller | 536/103 |
| 4,863,737 | 9/1989 | Stanley et al. | 424/440 |
| 4,870,060 | 9/1989 | Muller | 514/58 |
| 4,883,785 | 11/1989 | Chow et al. | 514/31 |
| 4,916,134 | 4/1990 | Heeres et al. | 514/252 |
| 4,983,586 | 1/1991 | Bodor | 514/58 |
| 4,990,337 | 2/1991 | Kurihara et al. | 424/427 |

FOREIGN PATENT DOCUMENTS

| | | | |
|---|---|---|---|
| 93/19061 | 9/1993 | WIPO | 514/59 |

OTHER PUBLICATIONS

Hostetler et al., "Effect of Cyclodextrin on the Pharmacology of Antifungal Oral Azoles", *Antimicrobial Agents And Chemotherapy*, Feb. 1992, pp. 477–480.

Pitha et al., "Preparation of drug:hydroxypropylcyclodextrin complexes by a method using ethanol or aqueous ammonium hydroxide as co-solubilizers", *International Journal of Pharmaceutics*, 80 (1992) 253–258.

*Primary Examiner*—James H. Reamer
*Attorney, Agent, or Firm*—Charles J. Metz

[57] ABSTRACT

The present invention concerns a formulation for oral administration comprising an antifungal, a sufficient amount of a cyclodextrin or a derivative thereof, an aqueous acidic medium as bulk liquid carrier and an alcoholic co-solvent Addition of one or more pharmaceutically acceptable sweeteners and one or more pharmaceutically acceptable flavors thereto yields palatable oral formulations. A process of preparing such formulations and pharmaceutical dosage forms comprising said formulations.

7 Claims, No Drawings

ORAL FORMULATIONS ON AN ANTIFUNGAL

CROSS-REFERENCE TO RELATED APPLICATIONS

This application is based upon PCT application Ser. No. PCT/EP 94/03169, filed Sep. 22, 1994, which claims priority from U.S. patent application Ser. No. 08/129,504, filed on Sep. 30, 1993 now abandoned.

The present invention is concerned with novel compositions of antifungal agents which have low solubility in aqueous media, a process for preparing said compositions and pharmaceutical dosage forms for oral administration comprising said novel compositions.

The development of efficacious pharmaceutical compositions of azole antifungals such as for example, itraconazole and saperconazole, is hampered considerably by the fact that said antifungals are only very sparingly soluble in water. The solubility and bioavailability of said compounds can be increased by complexation with cyclodextrins or derivatives thereof as described in WO 85/02767 and U.S. Pat. No. 4,764,604. Alternatively, strongly acidic formulations (pH≦1.5) of itraconazole and saperconazole can be formed in which the active ingredients are partially dissolved. Obviously such strongly acidic formulations are useless for oral administration. Aqueous formulations comprising a co-solvent such as PEG 400 completely dissolve itraconazole at pH 2.3–2.5. However, these acidic formulations have problems with regard to ease-of-preparation, acceptability, palatability and especially bioavailability: upon administration said formulations can precipitate irreversibly, e.g. in the stomach. Acidic formulations comprising cyclodextrin or a derivative thereof might appear an obvious alternative, but the mere combinations prove to suffer from a number of similar problems, in particular difficulty-of-preparation, lack of stability (shelf life) and palatability, and unreliable absorption. In short, there still exists an important demand for easily prepared formulations of antifungal agents with good bioavailability and acceptable organoleptic properties for oral administration.

The present invention relates to formulations for oral administration which comprise an antifungal, e.g. itraconazole or saperconazole, as active ingredient, a sufficient mount of a cyclodextrin or a derivative thereof as a solubilizer, an aqueous acidic medium as bulk liquid carrier and an alcoholic co-solvent that greatly simplifies the preparation of the composition. Preferred formulations are rendered more palatable by adding one or more pharmaceutically acceptable sweeteners, and one or more pharmaceutically acceptable flavours.

A low-dosage formulation according to the present invention is suitable for treating patients suffering from fungal infections, particularly for treating AIDS patients with oral candidiasis infections. The need for reliable formulations of itraconazole (and saperconazole) in this indication is especially high because of resistance to fluconazole developing in Candida strains. Generally, 400 mg/day represents the minimum dose required to obtain meaningful plasm levels. Suitable oral formulations typically comprise from about 0.5% to about 1.5% (w/v), preferably about 1% (w/v) of the active ingredient.

A high-dosage formulation according to the present invention is suitable for treating patients suffering from systemic fungal infections. Suitable oral formulations for combatting systemic fungal infections typically comprise from about 3% to about 5%, preferably about 4% (w/v) of the active ingredient.

The formulations of the present invention are also suitable for the treatment of fungal infections in non-human animals, in particular for the treatment of dermatophytoses.

Itraconazole or (±)-cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one, is a broadspectrum antifungal compound developed for oral, parenteral and topical use and is disclosed in U.S. Pat. No. 4,267,179. Its difluoro analog, saperconazole or (±)-cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]-phenyl]-2,4-dihydro-2-(1-methoxypropyl)-3H-1,2,4-triazol-3-one, has improved activity against Aspergillus spp. and is disclosed in U.S. Pat. No. 4,916,134.

Appropriate cyclodextrin derivatives are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD.

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. In the cyclodextrin derivatives for use in the compositions according to the present invention the M.S. is in the range of 0.125 to 10, in particular of 0.3 to 3, or from 0.3 to 1.5. Preferably the M.S. ranges from about 0.3 to about 0.8, in particular from about 0.35 to about 0.5 and most particularly is about 0.4. M.S. values determined by NMR of IR preferably range from 0.3 to 1, in particular from 0.55 to 0.75.

The average substitution degree (D.S.) refers to the average number of substituted hydroxyls per anhydroglucose unit. In the cyclodextrin derivatives for use in the compositions according to the present invention the D.S. is in the range of 0.125 to 3, in particular of 0.2 to 2 or from 0.2 to 1.5. Preferably the D.S. ranges from about 0.2 to about 0.7, in particular from about 0.35 to about 0.5 and most particularly is about 0.4. D.S. values determined by NMR of IR preferably range from 0.3 to 1, in particular from 0.55 to 0.75.

More particular β- and γ-cyclodextrin hydroxyalkyl derivatives for use in the compositions according to the present invention are partially substituted cyclodextrin derivatives wherein the average degree of alkylation at hydroxyl groups of different positions of the anhydroglucose units is about 0% to 20% for the 3 position, 2% to 70% for the 2 position and about 5% to 90% for the 6 position. Preferably the amount of unsubstituted β- or γ-cyclodextrin is less than 5% of the total cyclodextrin content and in particular is less than 1.5%. Another particularly interesting cyclodexuin derivative is randomly methylated β-cyclodextrin.

Most preferred cyclodextrin derivatives for use in the present invention are those partially substituted β-cyclodextrin ethers or mixed ethers having hydroxypropyl, hydroxyethyl and in particular 2-hydroxypropyl and/or 2-(1-hydroxypropyl) substituents.

The most preferred cyclodextrin derivative for use in the compositions of the present invention is hydroxypropyl-β-cyclodextrin having a M.S. in the range of from 0.35 to 0.50 and containing less than 1.5% unsubstituted β-cyclodextrin. M.S. values determined by NMR or IR preferably range from 0.55 to 0.75.

Substituted cyclodextrins can be prepared according to procedures described in U.S. Pat. No. 3,459,731, EP-A-0,149,197, EP-A-0,197,571, U.S. Pat. No. 4,535,152, WO-90/12035 and GB-2,189,245. Other references describing cyclodextrins for use in the compositions according to the present invention, and which provide a guide for the preparation, purification and analysis of cyclodextrins include the following: "Cyclodextrin Technology" by J ózsef Szejtli, Kluwer Academic Publishers (1988) in the chapter Cyclodextrins in Pharmaceuticals; "Cyclodextrin Chemistry" by M. L. Bender et at., Springer-Verlag, Berlin (1978); "Advances in Carbohydrate Chemistry", Vol. 12 Ed. by M. L. Wolfrom, Academic Press, New York (157) in the chapter The Schardinger Dextrins by Dexter French at p. 189–260; "Cyclodextrins and their Inclusions Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p. 343–361 (1981); A. P. Croft and R. A. Bartsch in Tetrahedron, 39, p. 1417–1474 (1983); Irie et al. Pharmaceutical Research, 5, p. 713–716, (1988); Pitha et al. Int. J. Pharm. 29, 73, (1986); DE 3,118,218; DE-3,317,064; EP-A-94,157; U.S. Pat No. 4,659,696; and U.S. Pat. No. 4,383,992. The low-dosage oral formulations according to the present invention typically comprise from about 20% to about 60% (w/v), preferably about 40% (w/v) of the cyclodextrin. The high-dosage formulations typically comprise from about 50% to about 80% (w/v), preferably about 60% (w/v) of the cyclodextrin derivative.

In order to increase the rate of dissolution of the poorly soluble antifungal during the manufacturing process, an alcoholic co-solvent is employed in the formulations according to the present invention. For this purpose, preference is given to those alcoholic co-solvents that have good dissolving power for itraconazole and/or saperconazole, in particular ethanol, propylene glycol and glycerol, especially propylene glycol. Without the alcoholic co-solvent, the dissolution of itraconazole or saperconazole in an aqueous acidic cyclodextrin medium is very slow, requiring a viscous suspension to be stirred for a prohibitively long time until complete dissolution is obtained. Addition of the alcoholic co-solvent, in the range of about 1% (v/v) to about 20% (v/v), preferably about 10% (v/v), increases the dissolution rate of the antifungal agent in an aqueous acidic cyclodextrin medium by a factor of at least 5 (when used at 10% (v/v)) and thus considerably shortens and simplifies the production process.

As a bulk liquid carrier there is used an acidic aqueous medium. Preferably the acidity of said carrier derives from a strong, pharmaceutically acceptable acid such as hydrochloric acid. The bioavailability of the antifungal agent and the organoleptic properties of the oral formulations are affected contrariwise by the acidity. An optimum effect can be obtained at pH 2.0±0.1: that is, at this pH value, a sufficiently stable and bioavailable antifungal formulation is obtainable, the organoleptic properties of which can be rendered acceptable.

Not surprisingly, the ingredients thus far described yield a fairly strong-tasting potion when mixed with one another. Besides the acid taste due to the low pH, a bitter taste originating from the active ingredient, and possibly from the co-solvent (e.g. in the case of propylene glycol), is also present. Optimum taste masking can be obtained by the use of two types of adjuvants, namely pharmaceutically acceptable sweeteners and flavours. Sweeteners are the more important additives in the low-dosage formulations, whereas the flavours are more important in the high-dosage formulations.

The pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

The intense sweetener is conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v). In the high-dosage formulations the cyclodextrin derivative behaves as a bulk sweetener and none of the aforementioned bulk sweeteners needs to be added.

The pharmaceutically acceptable flavours which can mask the bitter tasting ingredients in the low-dosage formulations are preferably fruit flavours such as cherry, raspberry, black currant or strawberry flavour. A combination of two cherry flavours was found to yield very good results in an itraconazole formulation both as regards physico-chemical stability as well as regards organoleptic acceptability. In the high-dosage formulations stronger flavours are required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

A preferred high-dosage formulation according to the present invention comprises by weight or by volume based on the total volume of the formulation:

(a) 4% (w/v) itraconazole;

(b) 60% (w/v) hydroxypropyl-β-cyclodextrin;

(c) 10% (v/v) propylene glycol;

(d) acid and base to adjust the pH of the composition within the range of 2.0±0.1;

(e) 0.08% (w/v) sodium saccharin;

(f) up to 1% (w/v) of one or more strong flavours; and (g) water.

The preparation of the formulations according to the present invention will hereafter be described with regard to a preferred low-dosage formulation having the following composition (% are by weight or by volume based on the total volume of the formulation):

(a) 1% (w/v) itraconazole;

(b) 40% (w/v) hydroxypropyl-β-cyclodextrin;

(c) 10% (v/v) propylene glycol;

(d) acid and base to adjust the pH of the composition within the range of 2.0±0.1;

(e) 0.06% (w/v) sodium saccharin;

(f) 19% (v/v) sorbitol (70%) non-crystallizing solution;

(g) up to 1% (w/v) of one or more cherry flavours; and (h) water.

Optionally, the above preferred low-dosage formulation further comprises up to 0.1%, in particular 0.02% caramel sweetener.

Similar formulations can be prepared with saperconazole, though other flavours may be preferred then.

Said process of preparation comprises the steps of (a) dissolving the active ingredient in the alcoholic co-solvent and acid;

(b) dissolving the cyclodextrin in water and adding thereto the solution prepared in (a) while stirring until homogenous;

(c) adding the sweetener(s) and the flavour(s);

(d) adjusting the acidity to pH 2.0±0.1 and (e) diluting the formulation to the desired end-volume.

In particular, for preparing 1 liter of the aforementioned preferred formulation 100 ml of propylene glycol is treated with 3.76 ml concentrated HCl, stirred and slightly heated. 10 g itraconazole is added and stirring is continued until homogeneous.

In a separate vessel, 400 g hydroxypropyl-β-cyclodextrin is dissolved in 400 ml distilled water. The solution of the active ingredient is added slowly to the cyclodextrin solution while stirring. The sorbitol solution (190 ml) is added and stirred till homogeneous. The sodium saccharin (0.6 g) is dissolved in 50 ml distilled water and added to the mixture. The flavours are added and the pH of the mixture (about 1.7) is adjusted with a 10N NaOH solution to pH 2.0±0.1. The resulting solution is diluted with distilled water to an end volume of 1 liter. A pharmaceutical dosage form is obtained by filtering the previous solution and filling it into suitable containers. e.g. in 100 ml glass bottles with a screw cap. The pharmaceutical dosage form advantageously comprises a minimal volume of air above the solution, preferably an inert gas such as nitrogen. Besides the exclusion of air (oxygen), storage at temperatures below 25° C. also beneficially affects the maximum shelf life of the formulation for oral administration.

In case a more simple formulation lacking the flavour(s) and/or sweetener(s) is envisaged, step (c) is omitted partially or completely from the process of preparation.

We claim:

1. A formulation for oral administration comprising:

(a) itraconazole or saperconazole;

(b) a sufficient amount of a hydroxypropyl-β-cyclodextrin having an M.S. in the range of 0.3 to 3 and containing less than 5% unsubstituted β-cyclodextrin, to act as a solubilizer for the itraconazole or saperconazole;

(c) an aqueous acidic medium as bulk liquid carrier;

(d) from about 1% (v/v) to about 20% (v/v) of an alcoholic co-solvent selected from the group consisting of ethanol, propylene glycol and glycerol;

(e) one or more pharmaceutically acceptable intense sweeteners plus one or more bulk sweeteners; and (f) one or more pharmaceutically acceptable flavors.

2. A formulation according to claim 1 wherein the cyclodextrin is hydroxypropyl-β-cyclodextrin having an M.S. in the range of 0.35 to 0.50 and containing less than 1.5% unsubstituted β-cyclodextrin.

3. A formulation according to claim 2 wherein the alcoholic co-solvent is propylene glycol.

4. A formulation according to claim 3 having a pH of 2.0±0.1.

5. A formulation according to claim 4 wherein the intense sweetener is selected from the group consisting of saccharin, sodium or calcium saccharin and the bulk sweetener is selected from the group consisting of sorbitol, mannitol, fructose, sucrose, maltose, glucose, caramel or honey.

6. A formulation according to claim 1 comprising by weight or by volume based on the total volume of the formulation:

(a) 4% (w/v) itraconazole;

(b) 60% (w/v) hydroxypropyl-β-cyclodextrin;

(c) 10% (v/v) propylene glycol;

(d) acid and base to adjust the pH of the composition within the range of 2.0±0.1;

(e) 0.08% (w/v) sodium saccharin;

(f) up to 1% (w/v) of one or more flavours; and (g) water.

7. A formulation according to claim 1 comprising by weight or by volume based on the total volume of the formulation:

(a) 1% (w/v) itraconazole or saperconazole;

(b) 40% (w/v) hydroxypropyl-β-cyclodextrin;

(c) 10% (v/v) propyleneglycol;

(d) acid or base to adjust the pH of the composition within the range of 2.0±0.1;

(e) 0.06% (w/v) sodium saccharin;

(f) 19% (v/v) sorbitol (70%) non-crystallizing solution;

(g) up to 1% (w/v) of one or more flavours;

(h) 0.02% (w/v) of a carmel sweetener; and (i) water.

* * * * *

(12) EX PARTE REEXAMINATION CERTIFICATE (5821st)
United States Patent
François et al.

(10) Number: US 5,707,975 C1
(45) Certificate Issued: Jul. 24, 2007

(54) ORAL FORMULATIONS ON AN ANTIFUNGAL

(75) Inventors: Marc Karel Jozef François, Kalmthout (BE); Willy Maria Albert Carlo Dries, Merksplas (BE)

(73) Assignee: Janssen Pharmaceutica N.V., Beerse (BE)

Reexamination Request:
No. 90/007,801, Nov. 9, 2005

Reexamination Certificate for:
Patent No.: 5,707,975
Issued: Jan. 13, 1998
Appl. No.: 08/604,950
Filed: Feb. 22, 1996

(22) PCT Filed: Sep. 22, 1994

(86) PCT No.: PCT/EP94/03169

§ 371 (c)(1),
(2), (4) Date: Feb. 22, 1996

(87) PCT Pub. No.: WO95/08993
PCT Pub. Date: Apr. 6, 1995

(51) Int. Cl.
*A61K 9/00* (2006.01)
*A61K 47/48* (2006.01)
*A61K 47/40* (2006.01)
*A61K 31/495* (2006.01)

(52) U.S. Cl. ................................. 514/58; 514/254.07
(58) Field of Classification Search ............ None
See application file for complete search history.

(56) References Cited

U.S. PATENT DOCUMENTS

| 4,160,827 A | * | 7/1979 | Cho et al. ................. 514/94 |
| 4,727,064 A | | 2/1988 | Pitha |
| 4,892,877 A | | 1/1990 | Sorrentino |
| 4,916,134 A | | 4/1990 | Heeres et al. |
| 5,024,997 A | | 6/1991 | Motola et al. |
| 5,120,720 A | | 6/1992 | Pitha et al. |
| 5,698,562 A | | 12/1997 | Mendes et al. |
| 5,707,975 A | | 1/1998 | François et al. |
| 5,998,413 A | | 12/1999 | Heeres et al. |

FOREIGN PATENT DOCUMENTS

| EP | 0219458 B1 | 4/1987 |
| EP | 0356254 A3 | 2/1990 |
| EP | 0556057 B1 | 8/1993 |
| GB | 810537 | 3/1959 |
| WO | WO 85/02767 | 7/1985 |
| WO | WO 93/09114 | 5/1993 |

* cited by examiner

*Primary Examiner*—Bennett Celsa

(57) ABSTRACT

The present invention concerns a formulation for oral administration comprising an antifungal, a sufficient amount of a cyclodextrin or a derivative thereof, an aqueous acidic medium as bulk liquid carrier and an alcoholic co-solvent Addition of one or more pharmaceutically acceptable sweeteners and one or more pharmaceutically acceptable flavors thereto yields palatable oral formulations. A process of preparing such formulations and pharmaceutical dosage forms comprising said formulations.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 6 and 7 are determined to be patentable as amended.

Claims 2–5, dependent on an amended claim, are determined to be patentable.

New claims 8 and 9 are added and determined to be patentable.

1. A formulation for oral administration comprising *by weight or by volume based on the total volume of the formulation*:
   (a) *from about 0.5% to about 1.5%* (w/v) itraconazole [or saperconazole];
   (b) [a sufficient amount of a] *from about 20% to about 60% (w/v)* hydroxypropyl-β-cyclodextrin having [an M.S.] *a molar substitution* in the range of 0.3 to 3 and containing less than 5% unsubstituted β-cyclodextrin, to act as a solubilizer for the itraconazole [or saperconazole];
   (c) an aqueous acidic medium as bulk liquid carrier;
   (d) from about 1% (v/v) to about 20% (v/v) of an alcoholic co-solvent selected from the group consisting of ethanol, propylene glycol and glycerol;
   (e) *from about 0.04% to about 0.1% (w/v) of* one or more pharmaceutically acceptable intense sweeteners [plus] *and from about 10% to about 35% (w/v) of* one or more bulk sweeteners; [and]
   (f) *up to 1% (w/v) of* one or more pharmaceutically acceptable flavors*; and*
   (g) water.

6. A formulation [according to claim 1] *for oral administration* comprising by weight or by volume based on the total volume of the formulation:
   (a) 4% (w/v) itraconazole;
   (b) 60% (w/v) hydroxypropyl-β-cyclodextrin *having a molar substitution in the range of 0.3 to 3 and containing less than 5% unsubstituted β-cyclodextrin*;
   (c) 10% (v/v) propylene glycol;
   (d) acid and base to adjust the pH of the composition within the range of 2.0±0.1;
   (e) 0.08% (w/v) sodium saccharin;
   (f) up to 1% (w/v) of one or more flavours; and
   (g) water.

7. A formulation [according to claim 1] *for oral administration* comprising by weight or by volume based on the total volume of the formulation:
   (a) 1% (w/v) itraconazole or saperconazole;
   (b) 40% (w/v) hydroxypropyl-β-cyclodextrin *having a molar substitution in the range of 0.3 to 3 and containing less than 5% unsubstituted β-cyclodextrin*;
   (c) 10% (v/v) [propyleneglycol] *propylene glycol*;
   (d) acid or base to adjust the pH of the composition within the range of 2.0±0.1;
   (e) 0.06% (w/v) sodium saccharin;
   (f) 19% (v/v) sorbitol (70%) non-crystallizing solution;
   (g) up to 1% (w/v) of one or more flavours;
   (h) 0.02% (w/v) of a caramel sweetener; and
   (i) water.

*8. A formulation for oral administration comprising by weight or by volume based on the total volume of the formulation:*
   *(a) 1% (w/v) itraconazole or saperconazole;*
   *(b) 40% (w/v) hydroxypropyl-β-cyclodextrin having a molar substitution in the range of 0.3 to 3 and containing less than 5% unsubstituted-β-cyclodextrin;*
   *(c) 10% (v/v) propylene glycol;*
   *(d) an aqueous acidic medium as bulk liquid carrier;*
   *(e) 0.06% (w/v) sodium saccharin;*
   *(f) 19% (v/v) sorbitol (70%) non-crystallizing solution;*
   *(g) up to 1% (w/v) of one or more flavours; and*
   *(h) water.*

*9. A formulation for oral administration comprising by weight or by volume based on the total volume of the formulation:*
   *(a) 1% (w/v) itraconazole;*
   *(b) 40% (w/v) hydroxypropyl-β-cyclodextrin having a molar substitution in the range of 0.3 to 3 and containing less than 5% unsubstituted-β-cyclodextrin;*
   *(c) 10% (v/v) propylene glycol;*
   *(d) an aqueous acidic medium as bulk liquid carrier;*
   *(e) 0.06% (w/v) sodium saccharin;*
   *(f) 19% (v/v) sorbitol (70%) non-crystallizing solution;*
   *(g) up to 1% (w/v) of one or more flavours;*
   *(h) 0.02% (w/v) of a caramel sweetener; and*
   *(i) water.*

\* \* \* \* \*